United States Patent [19]

Shemano

[11] 4,038,400

[45] July 26, 1977

[54] METHOD OF TREATING CONDITIONS OF DELAYED HYPERSENSITIVITY USING BIS-BASIC SUBSTITUTED ACENAPHTHENE DERIVATIVES

[75] Inventor: Irving Shemano, Cincinnati, Ohio

[73] Assignee: Richardson-Merrell Inc., Wilton, Conn.

[21] Appl. No.: 628,530

[22] Filed: Nov. 3, 1975

Related U.S. Application Data

[62] Division of Ser. No. 370,289, June 15, 1973, Pat. No. 3,937,842.

[51] Int. Cl.$^2$ .................. A61K 31/445; A61K 31/33; A61K 31/40

[52] U.S. Cl. .................. 424/267; 424/244; 424/274

[58] Field of Search .................. 424/244, 267, 274

[56] References Cited

U.S. PATENT DOCUMENTS

| | | | |
|---|---|---|---|
| 3,687,956 | 8/1972 | Zivkovic | 424/267 |
| 3,707,471 | 12/1972 | Albrecht et al. | 424/267 |

Primary Examiner—Sam Rosen
Attorney, Agent, or Firm—L. Ruth Hattan; Eugene O. Retter; George W. Rauchfuss, Jr.

[57] ABSTRACT

Novel 3,6-bis basic ketone derivatives of acenaphthene useful in treating conditions of delayed hypersensitivity are disclosed.

3 Claims, No Drawings

METHOD OF TREATING CONDITIONS OF DELAYED HYPERSENSITIVITY USING BIS-BASIC SUBSTITUTED ACENAPHTHENE DERIVATIVES

This application is a division of copending application Ser. No. 370,289, filed June 15, 1973, issued Feb. 10, 1976, as U.S. Pat. No. 3,937,842.

FIELD OF THE INVENTION

This invention relates to the use of bis-basic ketone derivatives of acenaphthene in treating conditions of delayed hypersensitivity.

The compounds of this invention are disclosed in copending application Ser. No. 317,148, filed Dec. 21, 1972, now U.S. Pat. No. 4,008,240.

The compounds of this invention are prepared from readily available acenaphthene. British Patent Specification 291,347 discloses a Friedel-Crafts preparation of a bis-(chloroacetyl)derivative of acenaphthene, having the reported configuration:

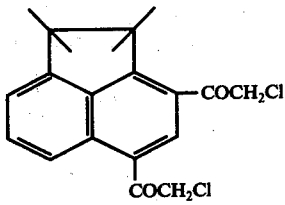
(I)

The closest prior art known to applicants, Chemical Abstracts 59, 12724a (1963), discloses a Friedel-Crafts diacetylation of acenaphthene in order to prepare a compound having the structure:

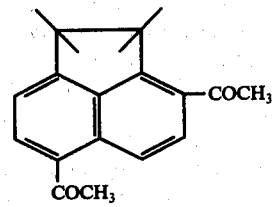
(II)

Although the abstract describes the compound as a 2,5-diacetyl derivative of acenaphthene, the presently recommended Chemical Abstracts nomenclature is that of a 3,6-diacetyl derivative of acenaphthene, the acenaphthene ring system being numbered as indicated below:

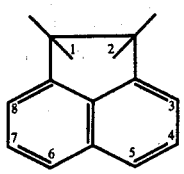
(III)

SUMMARY OF THE INVENTION

This invention relates to the use of new 3,6-bis-basic ketones of acenaphthene in treating conditions of delayed hypersensitivity. The compounds of the present invention may be represented by the following general formula:

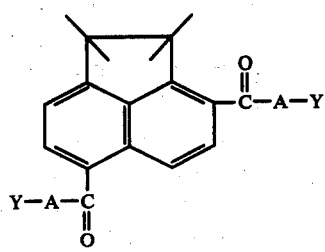
(IV)

wherein A is a straight or branched alkylene chain having from 1 to 6 carbon atoms; and Y is selected from the group consisting of:

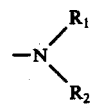

wherein $R_1$ and $R_2$ are individually selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group;

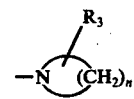

wherein n is an integer of from 4 to 6, and $R_3$ is selected from the group consisting of hydrogen, lower alkyl having from 1 to 4 carbon atoms, phenyl and benzyl in which said $R_3$ group is linked to any of the heterocyclic carbon atoms;

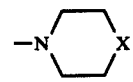

wherein X is selected from the group consisting of oxygen and $NR_4$, in which $R_4$ represents hydrogen or a lower alkyl group having from 1 to 4 carbon atoms; and the pharmaceutically acceptable acid addition salts thereof.

The compounds contemplated to be within the scope of the present invention as represented by formula (IV) include both the free base form as well as the pharmaceutically acceptable acid addition salts thereof. In general such salts are cyrstalline materials which are soluble in water and hydrophilic organic solvents and which are more stable than their corresponding free base forms. Certain salts, such as 3,6-bis(2-diethylaminoacetyl) acenaphthene dihydrochloride, have a tendency to absorb moisture and be hygroscopic in nature.

DETAILED DESCRIPTION OF INVENTION

As can be seen from the general formula (IV) above, the basic ketone groups,

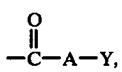

are linked to the tricyclic acenaphthene ring system by a replacement of the hydrogens in the 3- and 6-positions. Each basic ketone group consists of a basic amino function at its terminal end, separated from the acenaphthene nucleus by an alkylene chain of prescribed length, and connected to the aromatic nucleus by a ketone bridging function. It is also apparent that each basic ketone group is located on a benzenoid moiety of the aromatic nucleus.

One of the most convenient methods of obtaining the starting materials used in the preparation of the products of the present invention is via a Friedel-Crafts addition reaction to acenaphthene. The disubstituted 3,6-isomers are the isomers most commonly and readily obtained and are the particular position isomers described and claimed herein. It is probable that other methods of synthesis would provide additional position isomers which, in turn, would be expected to produce bis-basic ketones of acenaphthene which would be equally useful.

It is apparent from the general description of formula (IV) above, that compounds in which the symbol Y represents the groups:

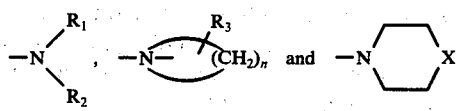

have the structures more fully shown by general formulas (V), (VI), and (VII) below. In each of the formulas A, $R_1$, $R_2$, $R_3$, X and $n$ have the meanings previously assigned.

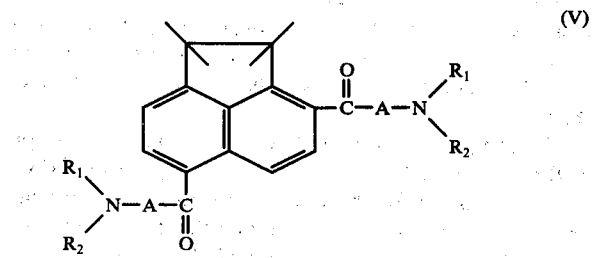

(V)

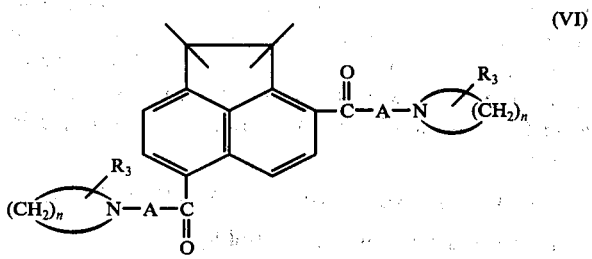

(VI)

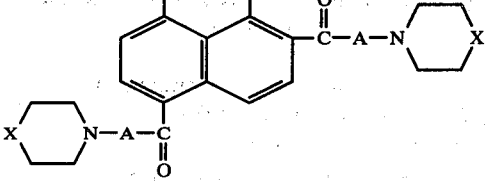

(VII)

The symbol A in each of the above formulas (IV), (V), (VI) and (VII) represents an alkylene group having from 1 to 6 carbon atoms and serves to separate the amino function from the ketone bridging function by at least one carbon atom. In other words the carbonyl oxygen and the amino nitrogen do not share the same carbon atom. Each alkylene group can be a straight or branched aliphatic chain and both alkylene groups can be the same or different. Preferably, however, the compounds of the present invention have alkylene groups which are both the same and which are straight aliphatic carbon chains. Illustrative of the various alkylene groups which are represented by the symbol -A- are: ethylene, 1,3-propylene, 1,4-butylene, 1,5-pentylene, 1,6-hexylene, 2-methyl-1,4-butylene and 3-methyl-1,5-pentylene.

Each of the amino groups represented by the symbol

in formula (V) above can be a primary, secondary or a tertiary amino. Preferably, both of the amine groups are the same and even more preferably they represent a tertiary amine. The symbols $R_1$ and $R_2$ can represent either hydrogen or a lower alkyl group. The term lower alkyl as used with regard to these amino groups relates to groups having from 1 to 6 carbon atoms. Illustrative of such groups are both straight or branched chain alkyl radicals such as: methyl, ethyl, propyl, isopropyl, n-butyl, sec.-butyl, isoamyl, n-pentyl and n-hexyl. When R and $R_1$ each represent a lower alkyl group, a preferred subgenus is formed.

The $R_1$ and $R_2$ groups may also represent an alicyclic or cycloalkyl group having from 3 to 6 carbon atoms. Illustrative of such groups are the cyclopropyl, cyclobutyl, cyclopentyl and cyclohexyl groups.

The term alkenyl used in reference to groups $R_1$ and $R_2$ of formula (V) above represents an unsaturated group having from 3 to 6 carbon atoms. Additionally, the unsaturation must reside in a position other than the 1-position of the alkenyl group. Illustrative of such groups are the allyl, 3-butenyl and the 4-hexenyl radicals.

Each of the heterocyclic groups of formula (VI), represented by the structure

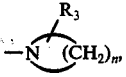

can be a monocyclic or a substituted monocyclic heterocyclic radical. Such groups typify saturated, monocyclic, heterocyclic radicals which are generally useful in lieu of the dilower alkylamino groups present in the compounds of the present invention and include heterocyclic 5, 6, or 7 membered rings, i.e., the symbol $n$ may be a whole integer of from 4 to 6. The $R_3$ substituent on the heterocyclic ring can be hydrogen, a straight or branched chain lower alkyl group having from 1 to 4 carbon atoms, the phenyl and benzyl radicals and may be present on any one of the heterocyclic carbon atoms. Illustrative of such heterocyclic radicals are the piperidino, 1-pyrrolidinyl, 3-methylpiperidino, 4-methylpiperidino, 4-tert-butylpiperidino, 4-benzylpiperidino and 4-phenylpiperidino radicals.

Each of the heterocyclic groups of formula (VII), represented by the structure

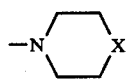

contains, in addition to the ring-containing nitrogen atom, a second hetero atom, represented by the symbol X, which can be either oxygen or another nitrogen atom in the form of the radical —$NR_4$. The symbol $R_4$ represents either hydrogen or a straight or branched chain lower alkyl radical having from 1 to 4 carbon atoms. Examples of heterocyclic radicals represented by this structure include the morpholino, piperazino, N-methylpiperazino, N-ethylpiperazino and N-isopropylpiperazino radicals.

Illustrative of the 3,6-bis-basic ketones of acenaphthene generally contemplated to be within the scope of formula (IV) are: 3,6-bis[2-(diethylamino)acetyl]acenaphthene, 3,6-[2-(dibutylamino)acetyl]acenaphthene, 3,6-bis[2-(dimethylamino)acetyl]acenaphthene, 3,6-bis[2-(diisopropylamino)acetyl]acenaphthene, 3,6-bis(2-piperidinoacetyl)acenaphthene, 3,6-bis[5-(dimethylamino)valeryl]acenaphthene, 3,6-bis[4-(diethylamino)butyryl]acenaphthene, 3,6-bis[2-(diallylamino)acetyl]acenaphthene, 3,6-bis[2-(dicyclohexylamino)acetyl]acenaphthene, 3,6-bis(4-morpholinobutyryl)acenaphthene, 3,6-bis[4-(4-methylpiperazino)butyryl]acenaphthene, 3,6-bis[5-(4-methylpiperidino)valeryl]acenaphthene and 3,6-bis(4-aminobutyryl)acenaphthene.

The expression "pharmaceutically acceptable acid addition salts" is intended to apply to any non-toxic organic or inorganic acid addition salts of the base compounds represented by formula (IV). Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono or the di-acid salts can be formed, and such salts can exist in either a hydrated or a substantially anhydrous form. In general, the acid addition salts of these compounds are crystalline materials which are soluble in water and various hydrophillic organic solvents and which in comparison to their free base forms, generally demonstrate higher melting points and an increased chemical stability.

The 3,6-bis-basic ketones of acenaphthene can be prepared using a variety of methods. The preferred method for the preparation of the instant compounds is to react a 3,6-bis(ω-haloacyl) derivative of acenaphthene with an amine or substituted amine in accordance with the following reaction scheme:

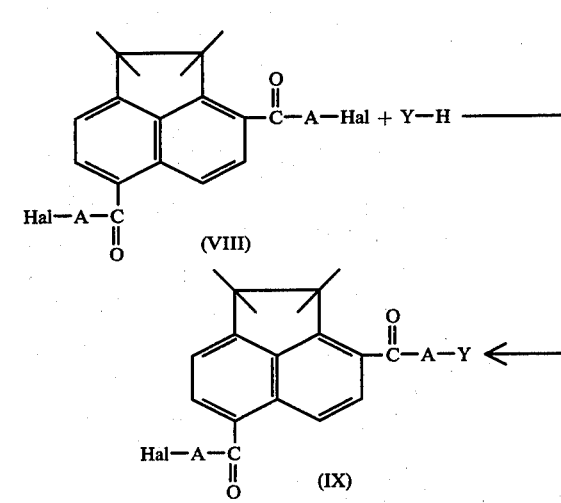

wherein A and Y have the meanings previously assigned, and Hal is either chlorine, bromine or iodine.

The 3,6-bis(ω-haloacyl) acenaphthene derivatives which are used as starting materials are readily obtained via a Friedel-Crafts acylation of acenaphthene. Suitable acylating agents which can be employed include chloroacetyl chloride, bromoacetyl bromide, 3-chloropropionyl chloride, 4-chlorobutyryl chloride, 5-chlorovaleryl chloride, 5-chloro-4-methylvaleryl chloride and 5-chloro-3-methylvaleryl chloride. The acylation reaction may be conducted in various solvents under catalysis using a variety of Lewis acids. The temperature and duration of the reaction may be varied to allow for optimum reaction conditions. A preferred procedure is to combine one equivalent of acenaphthene with 2.5 equivalents of the acylating agent dissolved in methylene chloride followed by the portionwise addition of 2.2 equivalents of aluminum chloride. Generally, the temperature of the reaction mixture is maintained at temperatures less than 0° C. Once the aluminum chloride addition has been completed, the temperature can be elevated from 25° to 40° C. to insure completion of the reaction. The reaction mixture is treated in the usual manner by decomposing the addition complex with ice water and hydrochloric acid. The product so obtained is recrystallized from methylene chloride, chloroform, methanol or methanolic mixtures of organic solvents. The procedure may also be varied such that there is a reverse addition of aromatic hydrocarbon and Lewis acid. The more reactive halogen derivative, that is, the bis(ω-iodoacyl)acenaphthene may be prepared from the corresponding bis(ω-chloroacyl) derivative using a halogen exchange reaction under the conditions generally employed in the Conant-Finkelstein reaction.

Of the typical amines useful in the above reaction sequence there can be mentioned, for example, ammonia, or a potential source of ammonia such as hexamethylene-tetramine, primary amines such as ethylamine or propylamine, and secondary amines, such as diethylamine, dibutylamine, piperidine, 4-methylpiperidine, morpholine, piperazine or N-ethylpiperazine.

The amination of bis(ω-haloacyl)acenaphthenes may be carried out under a variety of conditions. For example, the compound may be heated together with a large excess of the amine, the excess amine serving both as the reaction medium and the hydrohalide acceptor. This method is particularly suitable for those readily available amines, the excess of which can readily be removed from the reaction mixture as, for example, by distillation under reduced pressure or by washing the product with water. Alternatively, one equivalent of the 3,6-bis(ω-haloacyl)acenaphthene reactant may be heated with four equivalents of the amine using a variety of different types of organic solvents. For example, aromatic solvents such as benzene, toluene or xylene; ethers such as diethyl ether, tetrahydrofuran or dioxane; ketones such as acetone or butanone; aprotic solvents such as N,N-dimethylformamide, N,N-dimethylacetamide or dimethylsulfoxide; and mixtures of these solvents with water may all be utilized. When the reactant is a chloro-derivative, the reaction is frequently promoted by the addition of either sodium or potassium iodide, the iodide being used in either catalytic or stoichiometric amounts. In certain instances it may be advantageous to use only two equivalents of the amine, Y-H, for each equivalent of the 3,6-bis(ω-haloacyl)acenaphthene employed, using an excess of an inorganic base such as powdered sodium or potassium carbonate as a hydrohalide acceptor. The reaction normally proceeds in from about 12 hours to 14 days at temperatures ranging from about −30° to 150° C. Where volatile amines are employed, the reaction is best conducted under pressure in a suitable pressure reactor or autoclave; however, atmospheric or lower pressure may also be utilized.

Alternatively, the amination reaction can be conducted with a derivative of a 3,6-bis(ω-haloacyl)acenaphthene, such as a bis-ketal derivative. These derivatives are prepared by allowing a 3,6-bis(ω-haloacyl)acenaphthene to react with an excess of ethyl orthoformate in a polar solvent such as ethanol or tetrahydrofuran in the presence of an acid catalyst, such as hydrochloric acid, for several days. The 3,6-bis-basic ketones of acenaphthene are obtainable by subsequently hydrolyzing the aminoketal derivative using dilute acid.

The compounds of the present invention in which the symbol A represents an alkylene chain of from 3 to 6 carbon atoms can be prepared by the reaction of a Grignard reagent with a bis-ester of bis-amide of acenaphthene as represented in the following reaction sequence:

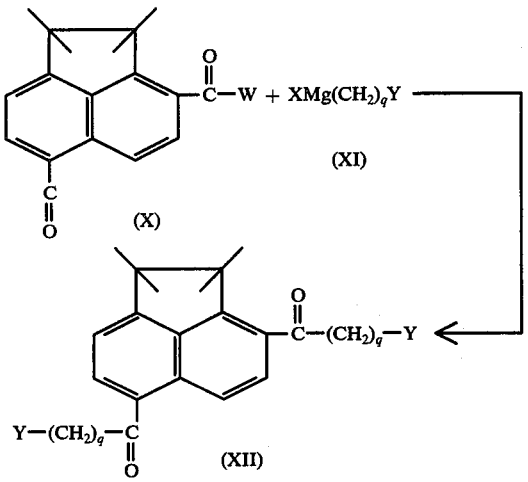

In the above reaction the symbol W is selected from the group consisting of:

a.

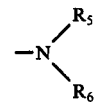

wherein $R_5$ and $R_6$ each represent hydrogen, lower alkyl having from 1 to 6 carbon atoms and when $R_5$ and $R_6$ are taken together with the nitrogen atom to which they are attached represent a saturated monocyclic heterocycle, and b. $OR_7$ wherein $R_7$ represents a straight or branched lower alkyl having from 1 to 6 carbon atoms, phenyl or benzyl;

X is bromine or chloride; $q$ is an integer of from 3 to 6; and Y is as previously defined with the further proviso that it may not include a hydrogen atom attached to the nitrogen atom.

The Grignard reaction proceeds in from about 1 to 24 hours at a temperature ranging from about −70° to about 80° C. The Grignard reagent, $XMg(CH_2)_q$-Y is prepared in the usual manner by the reaction of magnesium with an aminoalkyl halide, care being taken to exclude moisture. The acenaphthene bis-amides and bis-esters, which are used as starting materials for this reaction, are derived from 3,6-acenaphthene dicarboxylic acid using conventional methods known to those skilled in the art.

The compounds represented in general formula (IV) above, in which the symbol A represents ethylene, can also be prepared by means of a Mannich reaction as indicated in the following reaction sequence:

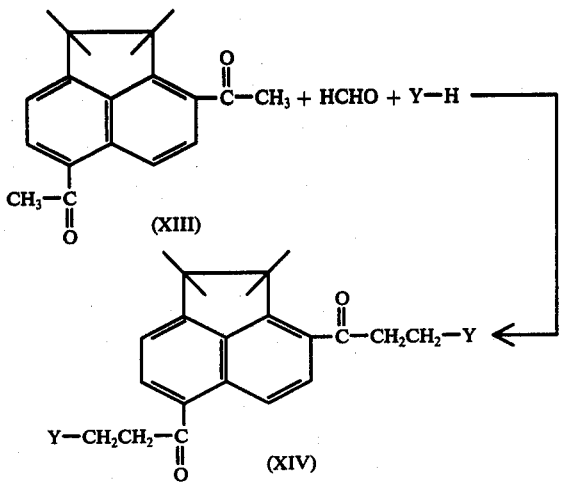

By combining one equivalent of 3,6-diacetylacenaphthene and two or more equivalents of an amine Y-H with three or more equivalents of formaldehyde, the condensation reaction will proceed in from about 1 to about 24 hours in solvents such as water, acetic acid, ethanol, butanol, dioxane and tetrahydrofuran. Generally, the condensation is conducted at temperatures equivalent to the reflux temperature of the solvent employed. Using this reaction either one of two sources of formaldehyde can be employed. If aqueous formalin is used as the formaldehyde source, the reaction can be conducted as a suspension with 3,6-diacetylacenaphthene. Alternatively, a co-solvent such as methanol may be added to allow the reaction to proceed in a homogeneous medium. If paraformaldehyde is the source of formaldehyde, the reaction can be conducted in any of the aforementioned organic solvents. It is frequently desirable to add a slight excess of hydrochloric acid to promote the depolymerization of paraformaldehyde either during the reaction or upon the completion of the reaction.

The secondary amine, Y-H, employed in the reaction may be added to the reaction medium as a hydrochloride salt or in the form of its free base with the hydrochloride salt being subsequently formed in situ by the addition of hydrochloric acid. Typical secondary amines which are employed in this reaction include dimethylamine, dubutylamine, piperidine, 4-methylpiperidine, morpholine and N-ethylpiperazine.

The 3,6-diacetylacenaphthene starting material can be prepared via the Friedel-Crafts acylation of acenaphthene itself or, alternatively, by means of a Grignard reaction using methylmagnesium halide on a 3,6-bis amide or bis ester of acenaphthene.

Introduction of an antigen, or a foreign substance, into an organism results in a specific immunological response changing the reactivity of the organism towards the antigen and substances closely resembling the antigen. This response is usually a heightened reactivity or increased resistance to the antigen. This heightened reactivity is due in part to the production of antibodies which can result in an immediate hypersensitivity and in part to a cell-mediated immunity which can result in delayed hypersensitivity. Cell-mediated immunity is dependent upon the presence of cells sensitized to antigen, primarily thymus-modified lymphocytes, which specifically interact with the antigen. Macrophages are also involved in the processing of antigen and in the effector mechanisms leading to delayed hypersensitivity.

The type of substances which elicit delayed hypersensitivity are many and various. They may be organic chemicals, including drugs, simple chemical derivatives, or protein-containing antigens of micro-organisms, such as, bacteria, viruses, fungi or protozoa, or tissue antigens. Conditions of delayed hypersensitivity are associated with numerous pathological disorders, for example, contact hypersensitivity in the skin, rejection of tissue grafts or transplants, autoimmune diseases and certain infectious diseases. Such pathological disorders often involve, in addition to the cell-mediated delayed hypersensitivity responses, humoral antibody responses involving the production of antigen-specific antibodies. Generally, treatment of these disorders has been with immunosuppressive agents, such as, purine analogs, folic acid antagonists, alkylating agents and corticosteroids. Such agents have been found to be non-specific in their immunosuppressant effects, that is, they suppress both the humoral antibody and delayed (cell-mediated) hypersensitivity responses. [Drug Therapy 1, no. 4, pp. 3–16 (1971)]. The compounds disclosed herein are unique in that they suppress only the delayed hypersensitivity response without concurrent suppression of the humoral immune response.

The compounds disclosed herein suppress delayed hypersensitivity responses thereby rendering the compounds useful in patients in the treatment of conditions of delayed hypersensitivity resulting from infectious diseases, specifically tuberculosis, streptococcus, staphylococcus and pneumococcus diseases, typhoid fever, undulant fever, chancroid, whooping-cough and leprosy; toxoids and vaccines, particularly diphtheria toxoid and smallpox vaccination; contact hypersensitivity in the skin, specifically from nickel salts, primrose or poison ivy, poison oak and paraphenylene diamine; rejection of tissue grafts and transplants; and autoimmune diseases, specifically rheumatoid arthiritis, systemic lupus erythematosus, glomerular nephritis, rheumatic fever, ulcerative colitis, diabetes mellitus, pernicious anemia, coeliac disease, primary atypical pneumonia, Hashimoto's thyroiditis, multiple sclerosis, peripherial neuritis, pemphigus, Addison's disease and Grave's disease.

The utility of the compounds disclosed herein in the treatment of conditions of delayed hypersensitivity is manifested by the ability of the compounds to suppress delayed hypersensitivity reactions in vitro in the macrophage migration inhibition test (MMIT) and in vivo in the experimental allergic encephalomyelitis (EAE) test, which are well recognized tests for detecting agents or compounds effective in treating conditions of delayed hypersensitivity, *Immunology for Students of Medicine*, 3rd edition, 1970, F. A. Davis Company, pp. 498–500; Federation Proceedings 27, No. 1, pp. 3–15, (1968); Advances in Immunology 5, pp. 131–208 (1966).

As used herein, the term patient means warm blooded animals, particularly mammals and humans. The compounds disclosed herein may be administered to a patient orally, parenterally, or topically either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions or emulsions for oral and parenteral administration. The quantity of compound administered can vary over a wide range to provide from about 0.1 mg/kg (milligrams per kilogram) to about 200 mg/kg of body weight of the patient per day, and preferably from about 1 mg/kg to 100 mg/kg of body weight of the patient per day, to achieve the desired effect. Unit doses can contain from about 5 mg to 1.0 g of a compound of this invention and may be administered, for example, from 1 to 4 times daily.

The invention described herein is more particularly illustrated by means of the following specific examples:

EXAMPLE I 3,6-Bis(2-chloroacetyl)acenaphthene

To a solution of 77.1 g (0.5 mole) of acenaphthene and 141.1 g (1.25 mole) of chloroacetyl chloride in 3 liters of methylene chloride which has been chilled to $-20°$ C., is added 146.7 g (1.1 mole) of aluminum chloride in increments with stirring. The temperature is maintained below $-10°$ C. during addition, stirred in the cold for an additional 2 hours and allowed to warm slowly to room temperature. The mixture is refluxed for an additional 4 hours, cooled overnight and cautiously poured into 3 liters of ice water. The resulting layers are separated and the organic layer washed with a dilute hydrochloric acid solution followed by a wash with a saturated sodium chloride solution. The methylene chloride layer is separated, dried over anhydrous magnesium sulfate, treated with charcoal, filtered and the filtrate is concentrated to a small volume. The resulting solid so obtained is filtered, washed and air dried, m.p. 184°–187° C. Recrystallization from hot acetone results in a product having a m.p. 188°–191° C. Its NMR spectrum identified the compound as 3,6-bis(2-chloroacetyl)acenaphthene.

EXAMPLE II 3,6-Bis[2-(diethylamino)acetyl]acenaphthene dihydrochloride

A mixture of 30.7 g (0.1 mole) of 3,6-bis(2-chloroacetyl)acenaphthene, 100 ml of diethylamine and 2 g of potassium iodide is dissolved in 500 ml of tetrahydrofuran and allowed to stand in a stoppered flask for 8 days. The resulting amine salt which forms is filtered, washed with tetrahydrofuran and the combined filtrates reduced to dryness in vacuo. The residue is dissolved in methylene chloride, treated with charcoal and acidified using ethereal hydrochloric acid. The resulting solid which forms is filtered, recrystallized from a methanol-ether solution and further recrystallized from a methanol-ethyl acetate solution to yield a product, hygroscopic in nature, which indicated by its analysis to be a tetrahydrate having a m.p. 220.5°–222° C. (dec), $\lambda_{max}$ (EtOH) 283.

EXAMPLE III

In accordance with the procedure described in Example I, but substituting for the chloroacetyl chloride the appropriate molar equivalent amounts of bromoacetyl bromide, 3-chloropropionyl chloride, 4-chlorobutyryl chloride, 5-chloro-4-methylvaleryl chloride and 5-chlorovaleryl chloride the following compounds are respectively obtained: 3,6-bis(2-bromoacetyl)acenaphthene, 3,6-bis(3-chloropropionyl)acenaphthene, 3,6-bis(4-chlorobutyryl)acenaphthene, 3,6-bis(5-chloro-4-methylvaleryl)acenaphthene.

EXAMPLE IV

In accordance with the procedure for Example II, but substituting for diethylamine the appropriate molar equivalent amounts of piperidine, dimethylamine, morpholine, diallylamine and dibutylamine, the following compounds are obtained, respectively: 3,6-bis(2-piperidinoacetyl)acenaphthene dihydrochloride hydrate, M.P. 275°–278° C, 3,6-bis[2-(dimethylamino)acetyl]acenaphthene dihydrochloride hydrate, M.P. 273°–276° C, 3,6-bis(2-morpholinoacetyl)acenaphthene dihydrochloride, 3,6-bis[2-(diallylamino)acetyl]acenaphthene dihydrochloride and 3,6-bis[2-(dibutylamino)acetyl]acenaphthene dihydrochloride.

EXAMPLE V

Following the procedure in Example II, but substituting an equivalent amount of 3,6-bis(3-chloropropionyl)acenaphthene for 3,6-bis(2-chloroacetyl)acenaphthene, the compound 3,6-bis[3-(diethylamino)propionyl]acenaphthene dihydrochloride is obtained.

EXAMPLE VI 3,6-Bis[4-(diethylamino)butyryl]acenaphthene dihydrochloride

A mixture of 36.1 g (0.10 mole) of 3,6-bis(4-chlorobutyryl)acenaphthene, 2 g of potassium iodide, 100 ml of diethylamine and 100 ml of tetrahydrofuran is placed in a bomb and heated for 24 hours at 120° C. Upon cooling, the mixture is filtered and the filtrate evaporated to dryness. The cooled residue is dissolved in 300 ml of 10% hydrochloric acid, filtered and the acid filtrate made alkaline with a 20% sodium hydroxide solution. The resulting 3,6-bis[4-(diethylamino)butyryl]acenaphthene so obtained is filtered and subsequently recrystallized from a methanol-ethyl acetate solution.

Following the above procedure but substituting an equivalent amount of 3,6-bis(5-chlorovaleryl)acenaphthene for the 3,6-bis(4-chlorobutyryl)acenaphthene, results in the preparation of the compound 3,6-[5-(diethylamino)valeryl]acenaphthene.

Following essentially the same procedure but substituting the appropriate molar equivalent amounts of pyrrolidine, morpholine, 4-methylpiperidine and 3-methylpiperidine for the diethylamine above, results in the formation of the following 3,6-bis-basic ketones of acenaphthene: 3,6[4-(1-pyrrolidinyl)butyryl]acenaphthene, 3,6-bis(4-morpholinobutyryl)acenaphthene, 3,6-bis[4-(4-methylpiperidino)butyryl]acenaphthene and 3,6-bis[4-(3-methylpiperidino)butyryl]acenaphthene.

EXAMPLE VII

The following Example is illustrative of the antiviral activity for the compounds of the present invention.

Thirty mice each weighing approximately 18 to 20 gms are divided into two groups, a control group containing 20 aminals and a test group of 10 animals. All of the animals are challenged with a fatal dose ($4LD_{50}$) of encephalomyocarditis virus. The test group of animals are treated prophylactically using a parenteral composition containing 3,6-bis[2-(diethylamino)acetyl]acenaphthene dihydrochloride tetrahydrate as the active ingredient dissolved in an aqeous solution of 0.15% hydroxyethylcellulose. The composition contains the active ingredient in an amount such that each dosage contains 0.25 ml which is equivalent to a dose level of 250 mg per kg. The control group receives a subcutaneous placebo containing the same volume of vehicle without, of course, the active ingredient. Observations over a ten day period show a termination of all the control animals within a period of from 4 to 5 days, with the treated group of animals surviving for a statistically longer period of time.

EXAMPLE VIII

Preparation of a capsule formulation

An illustrative composition for hard gelatin capsules is prepared as follows:

|   |   | Per Capsule |
|---|---|---|
| (a) | 3,6-Bis[2-(diethylamino)acetyl] acenaphthene dihydrochloride | 200 mg |
| (b) | Talc | 35 mg |

The formulation is prepared by passing the dry powders through a fine mesh screen and mixing them well. The powder is then filled into No. 0 hard gelatin capsules at a net fill of 235 mg per capsule.

Similarly, a soft gelatin capsule can be prepared in which the talc is omitted. The capsule can be filled directly with the dry 3,6-bis[2-(diethylamino)acetyl]acenpahthene dihydrochloride powder as a granulation, slug or compressed tablet using a rotary die or plate mold in which the soft gelatin capsule is formed.

EXAMPLE IX

Preparation of a tablet formulation

An illustrative composition for tablets is as follows:

|   |   | Per Tablet |
|---|---|---|
| (a) | 3,6-bis[2-(dimethylamino)acetyl] acenaphthene dihydrochloride | 100 mg |
| (b) | Wheat starch | 15 mg |
| (c) | Lactose | 33.5 mg |
| (d) | Magnesium stearate | 1.5 mg |

A granulation is prepared by mixing the lactose with the starch and granulated starch paste. The granulation is screened and mixed with the 3,6-bis[2-(dimethylamino)acetyl]acenaphthene dihydrochloride and magnesium stearate. The mixture is compressed in tablets weighing 150 mg each.

EXAMPLE X

Preparation of a pill formulation

An illustrative composition for pills is as follows:

|   |   | Per Pill |
|---|---|---|
| (a) | 3,6-bis(2-piperidinoacetyl) acenaphthene dihydrochloride | 100 mg |
| (b) | Starch, corn | 90 mg |
| (c) | Liquid glucose | 20 mg |

The pills are prepared by blending the active ingredient with the corn starch, adding the liquid glucose, and forming a plastic mass through a kneading action. The pills are cut and formed from the plastic pill mass.

EXAMPLE XI

Preparation of parenteral formulation

The following aqueous emulsion illustrates a useful parenteral composition:

| Each ml Contains | Ingredients | Amount |
|---|---|---|
| 50 mg | 3,6-bis[5-(diethylamino)valeryl]acenaphthene | 1.000 g |
| 100 mg | Polyoxyethylene sorbitan monooleate | 2.000 g |
| 0.0064 | Sodium chloride | 0.128 g |
|   | Water for injection, q.s. | 20.000 ml |

The above composition is prepared by preparing a solution of 0.64 g of sodium chloride in 100 ml of water suitable for injection. The polyoxyethylene sorbitan monooleate is mixed with the 3,6-bis[5-(diethylamino)valeryl]acenaphthene and a sufficient amount of the sodium chloride solution is added to the active ingredient and polyoxyethylene sorbitan monooleate to make 20 ml. The solutions are shaken and autoclaved for 20 minutes at 110° C. at 15 p.s.i.g. steam pressure. The resulting composition can be dispensed in a single ampule for multiple dosage or as 1 ml ampules for single dosages.

I claim:

1. A method of treating conditions of delayed hypersensitivity which comprises administering to a patient in need thereof a 3,6-bis-basic ketone of acenaphthene having the formula:

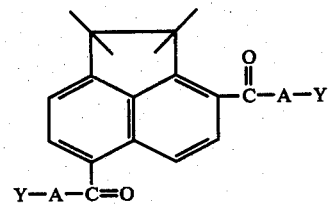

wherein A is a straight or branched alkylene chain having from 1 to 6 carbon atoms; and Y is the group

wherein $n$ is an integer of from 4 to 6, and $R^3$ is selected from the group consisting of hydrogen, lower alkyl having from 1 to 4 carbon atoms, phenyl and benzyl in which said $R^3$ group is linked to any of the heterocyclic carbon atoms; and pharmaceutically acceptable salts thereof in an amount effective to suppress delayed hypersensitivity.

2. A method of claim 1 wherein $n$ is the integer 5.

3. A method of claim 2 wherein the compound is 3,6-bis(2-piperidinoacetyl)acenaphthene and pharmaceutically acceptable salts thereof.

* * * * *

UNITED STATES PATENT OFFICE
CERTIFICATE OF CORRECTION

PATENT NO. : 4,038,400

DATED : July 26, 1977

INVENTOR(S) : Irving Shemano

It is certified that error appears in the above-identified patent and that said Letters Patent are hereby corrected as shown below:

Column 2, line 57 ...cyrstalline... should read --crystalline--.
Column 7, line 65 ...bis-ester of bis-amide... should read --bis-ester or bis-amide--. Column 8, line 44 ...chloride... should read --chlorine--. Column 13, line 28 ...acenpahthene... should read --acenaphthene--.

Signed and Sealed this

Second Day of May 1978

[SEAL]

Attest:

RUTH C. MASON
Attesting Officer

LUTRELLE F. PARKER
Acting Commissioner of Patents and Trademarks